United States Patent
Bhojaraja et al.

(10) Patent No.: US 11,996,180 B2
(45) Date of Patent: *May 28, 2024

(54) ENABLING THE USE OF MULTIPLE PICTURE ARCHIVING COMMUNICATION SYSTEMS BY ONE OR MORE FACILITIES ON A SHARED DOMAIN

(71) Applicant: CERNER INNOVATION, INC., North Kansas City, MO (US)

(72) Inventors: Kiran Bhojaraja, Bengaluru (IN); Deepak Gupta, K R Puram Hobli (IN); Vikram Nandwani, CV Raman Nagar (IN); Premjit Adhikary, Bongaigaon (IN); Tania Bhattacharyya, Ramamurthynagar (IN); Bobbie Milne, Kansas City, MO (US)

(73) Assignee: Cerner Innovation, Inc., Kansas City, MO (US)

(*) Notice: Subject to any disclaimer, the term of this patent is extended or adjusted under 35 U.S.C. 154(b) by 115 days.

This patent is subject to a terminal disclaimer.

(21) Appl. No.: 17/722,862

(22) Filed: Apr. 18, 2022

(65) Prior Publication Data

US 2022/0238206 A1 Jul. 28, 2022

Related U.S. Application Data

(63) Continuation of application No. 16/720,482, filed on Dec. 19, 2019, now Pat. No. 11,335,452.

(51) Int. Cl.
*G16H 30/20* (2018.01)
*G06F 21/62* (2013.01)
(Continued)

(52) U.S. Cl.
CPC ......... *G16H 30/20* (2018.01); *G06F 21/6245* (2013.01); *G16H 15/00* (2018.01); *G16H 30/40* (2018.01)

(58) Field of Classification Search
CPC .................. G06Q 50/22–24; G16H 30/20
See application file for complete search history.

(56) References Cited

U.S. PATENT DOCUMENTS 6,766,297 B1* 7/2004 Lamer ............... G06F 16/93
704/270
7,487,155 B2* 2/2009 Jebens ............ H04N 1/00132
(Continued)

OTHER PUBLICATIONS

"Can a Cloud PACS Be Used by Different Doctors Simultaneously", Trachtman; Purview; Mar. 14, 2017 (Year: 2017).*
(Continued)

*Primary Examiner* — John A Pauls
(74) *Attorney, Agent, or Firm* — Invoke

(57) ABSTRACT

Methods, systems, and computer-storage media are provided for utilizing multiple Picture Archiving Communication Systems (PACS) to view one more medical images by storing one or more PACS at a database within the system. Requests are received from one or more users at one or more facilities to utilize one or more PACS to view one or more medical images. After accessing the database to determine one or more PACS authorized for each facility from which a request is received, one or more users are provided with one or more PACS to view medical images associated with radiological exams and provide the necessary assessments and reports for treatment.

20 Claims, 9 Drawing Sheets

(51) Int. Cl.
 *G16H 15/00* (2018.01)
 *G16H 30/40* (2018.01)

(56) References Cited

U.S. PATENT DOCUMENTS

| | | | |
|---|---|---|---|
| 8,945,066 B2 | 2/2015 | Bochenko et al. | |
| 9,053,520 B2 | 6/2015 | Vik et al. | |
| 9,555,191 B2 | 1/2017 | Edwards et al. | |
| 2002/0035634 A1* | 3/2002 | Smolarski-Koff | G16H 30/20 709/230 |
| 2002/0050462 A1 | 5/2002 | Penney et al. | |
| 2005/0216314 A1* | 9/2005 | Secor | G16H 10/60 705/3 |
| 2009/0112882 A1* | 4/2009 | Maresh | G16H 10/60 |
| 2009/0128330 A1 | 5/2009 | Monroe | |
| 2011/0246239 A1* | 10/2011 | Vdovjak | G16H 40/67 705/3 |
| 2013/0151286 A1* | 6/2013 | Kablotsky | G16H 30/20 705/3 |
| 2013/0245545 A1 | 9/2013 | Arnold et al. | |
| 2014/0114672 A1* | 4/2014 | Wright | G16H 30/20 705/2 |
| 2014/0142980 A1* | 5/2014 | Revell | G06F 16/50 705/3 |
| 2014/0257847 A1* | 9/2014 | Hu | A61B 5/742 705/3 |
| 2015/0085066 A1* | 3/2015 | Desai | G16H 30/40 348/14.08 |
| 2015/0105903 A1 | 4/2015 | Denny et al. | |
| 2015/0251839 A1 | 9/2015 | Denny et al. | |
| 2015/0343151 A1 | 12/2015 | Stefansen | |
| 2016/0067418 A1 | 3/2016 | Morris et al. | |
| 2016/0378917 A1* | 12/2016 | Sharafshahi | G16H 30/20 705/2 |
| 2019/0156241 A1* | 5/2019 | Hughes | G06F 16/538 |
| 2021/0193296 A1 | 6/2021 | Bhojaraja et al. | |

OTHER PUBLICATIONS

Trachtman, Les, "Can a Cloud PACS Be Used by Different Doctors Simultaneously", Purview, Available online at: <https://www.purview.net/blog/can-a-cloud-pacs-be-used-by-different-doctors-simultaneously>, Mar. 14, 2017, 4 pages.

* cited by examiner

VDI CONFIGURATION

| NAME | VDI MODE | ORDER ID | PATH | FACILITY |
|---|---|---|---|---|
| PACS A | BIDIRECT... ▽ | 123456789ABC | C:\PROG... BROWSE | ALL ▽ |

Facility dropdown:
- ☑ ALL
- ☑ FACILITY 1
- ☑ FACILITY 2
- ☑ FACILITY 3
- ☑ FACILITY 4
- ☑ FACILITY 5
- ☑ FACILITY 6
- ☑ FACILITY 7
- ☑ FACILITY 8

Buttons: ADD | DELETE | ADD EMR PACS | OK | CANCEL | APPLY

*FIG. 4.*

| ☐ VDI CONFIGURATION | | | | | — ☐ ✕ |
|---|---|---|---|---|---|
| HELP 502 | 504 | 508 | 510 | 512 | |
| NAME | VDI MODE | ORDER ID | PATH | FACILITY | ☐ |
| PACS A | BIDIRECT... ▽ | 123456789ABC | C:\PROG... BROWSE | ALL ▽ | ☐ |
| PACS B | UNIDIRECT... ▽ | 123456789ABC | C:\PROG... BROWSE | FACILITY 1, 2, 3 ▽ | ☐ |
| PACS C | BIDIRECT... ▽ | | BROWSE | FACILITY 4, 5, 6 ▽ | ☐ |

ADD  DELETE  ADD EMR PACS 522  OK  CANCEL  APPLY 516, 518, 520

ENABLING THE USE OF MULTIPLE PICTURE ARCHIVING COMMUNICATION SYSTEMS BY ONE OR MORE FACILITIES ON A SHARED DOMAIN

CROSS-REFERENCE TO RELATED APPLICATIONS

This application having and entitled "Enabling The Use of Multiple Picture Archiving Communication Systems by One or More Facilities on a Shared Domain" is a continuation application of U.S. Non-Provisional application Ser. No. 16/720,482, filed on Dec. 19, 2019, and entitled "Enabling The Use of Multiple Picture Archiving Communication Systems by One or More Facilities on a Shared Domain." The entirety of the aforementioned application is incorporated by reference herein.

BACKGROUND

Over the years, the cost of healthcare has increased significantly and the management of individual healthcare has become more complex. In the course of treating individuals for various healthcare problems, healthcare providers frequently order radiological examinations for diagnostic and treatment purposes. Once a radiological exam, such as an x-ray, is conducted, a radiologist receives a request to review the image generated by the radiological exam. The radiologist, who may or may not be located at the facility where the radiological exam is taking place, then utilizes a Picture Archiving Communication Systems (PACS) to view the medical image and generate a report indicating the radiological findings. There are multiple different types of PACS available for viewing different types of radiological examinations.

To decrease costs, various elements of healthcare management are outsourced to healthcare providers, such as radiologists, who may not be physically onsite at a facility. Additionally, more than one facility may share a domain to further reduce costs. Currently, healthcare management systems are configured to allow the use of only one type of PACS for each domain, which limits the ability of radiologists to view different medical images via different PACS. As such, a system that would allow for the use of different PACS within a domain, would provide greater flexibility to radiologists viewing and analyzing radiological exams. Further, such a system would also be cost effective as it would allow different facilities within one domain to utilize different PACS and make it easier for radiologists viewing images remotely to utilize a variety of different PACS for different facilities to review medical images and provide assessments.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Various types of radiological exams are a critical and regular component of managing the healthcare of an individual. Radiological exams are used to diagnose the cause of symptoms presented, monitor how an individual's body is responding to treatment, and screen for different illnesses such as cancer or heart disease. As technology has progressed over the years, there are numerous types of radiological exams available for a variety of needs. Some examples of common radiological examinations utilized regularly are x-rays, magnetic resonance imaging (MRIs), computed tomography scan (CT or CAT scan), fluoroscopy, mammography, nuclear medicine (e.g. bone scans), positron emission tomography (PET scan), and ultrasounds. Each type of radiological exam may require a different type of PACS to view the image. PACS is medical imaging technology that provides economical storage and convenient access to images from multiple modalities. Electronic images and reports are transmitted digitally via PACS, which eliminates the need to manually file, retrieve or transport radiological images. Combined with available and emerging technology, PACS has the ability to deliver timely and efficient access to images, interpretations, and related data. PACS also reduces the physical and time barriers associated with traditional film-based image retrieval, distribution, and display.

In some instances, a PACS may be configured to produce images for various radiological exams. In other instances, each PACS could be customized to be used for a specific type of radiological image. As such, when a radiologist views the medical images generated from the radiological exam, the radiologist may need to utilize more than one type of PACS to review the image and make their medical assessments. Further, each radiologist may also have a preferred PACS for viewing and analyzing images based on the PACS technology or personal preference.

Currently, configurations of all PACS are stored in a system registry which imposes the restriction that only one PACS can be utilized per domain. Multiple facilities often share domains in order to reduce the cost of operating a domain. For example, small community hospitals within one region may share a common domain to decrease costs. As such, if three community hospitals are sharing the same domain, each hospital must use the same PACS to view radiological medical images. This limitation presents challenges for radiologist who may have preferred PACS for viewing medical images and making assessments or if certain PACS have limitations in their capabilities. Further, facilities may prefer to use different PACS based on the cost associated with each PACS. As such, the current configuration limiting the facilities sharing a domain to one PACS may increase costs for certain facilities. Additionally, the limitation of utilizing only one PACS per domain may also hinder the quality of the medical images viewed and the potential medical assessments made. Some PACS programs may have better technology or may be more optimal for use for certain x-rays. For example, a PACS utilized to view mammograms, x-rays, and ultrasounds may not be the best PACS for viewing more complex imaging such as PET or MRI scans.

PACS utilized by radiologists may be utilized via a radiologist desktop (RDT) application or the electronic medical record (EMR) application. For example, from the EMR, a radiologist may launch an PACS associated with the EMR for viewing the image. However, in the current configuration, if the EMR's PACS is utilized, no other $3^{rd}$ party PACS can be utilized. Once again, this presents limitations on radiologists and facilities who may need or want to utilize different PACS for the review of different types of medical images. In aspects where the PACS is launched on an RDT application, the RDT application may communicate with the EMR to deliver reports or other medical data associated with the assessment of the medical image reviewed.

At a high level, the present disclosure discloses the configuration of the PACS at the database level rather than the registry level within a domain. By changing where each of the PACS are stored from the registry level to the database level, multiple PACS can be utilized by different facilities within one shared domain. Each PACS is stored as a key value pair associated with each authorized facility in the database. Each PACS that is configured is associated with specific facilities, which allows radiologists at each facility to access the PACS that are approved for the individual facility. This also allows the radiologists to toggle between different PACS as needed. As a result, this new configuration eliminates the previous restrictions where only one PACS could be utilized by all facilities within a domain and allows for the use of both a $3^{rd}$ party PACS and EMR specific PACS.

Aspects herein describe computer-storage media, computerized methods, and computing systems that allow healthcare providers, such as radiologists, to utilize multiple PACS to view different medical images. The system comprises receiving an indication to launch a radiology desktop (RDT) application on a first user interface at a first facility. Then the system receives a request from the user to utilize one or more PACS to view one or more medical images. In response, a database is accessed to identify one or more PACS authorized for use at the first facility. The first user is then provided, via the first user interface of the RDT, with a first PACS authorized for use by the first user at the first facility. The first user is also provided with a second PACS, via the first user's interface of the RDT application, for use by the first user at the first facility.

As well, aspects herein are also directed to a system that comprises a database comprising one or more PACS configured to capture, store, and display one or more medical images on one or more user interfaces associated with one or more facilities. The system also comprises one or more processors and a storage device storing a computer program product comprising computer instructions that, upon execution by the one or more processors, cause the one or more processors to perform operations comprising receiving a first indication to launch a RDT application on a first user interface at a first facility and a second indication to launch a RDT application on a second user interface at a second facility. Then, the system receives a first request from the first user to utilize one or more PACS to view one or more medical images and a second request from the second user to utilize one or more PACS to view one or more medical images. The system accesses the database to identify one or more PACS authorized for the first user at the first facility and the second user at the second facility. Once the authorized PACS are identified, the system provides the first user with one or more PACS authorized for use by the first user at the first facility and the second user with one or more PACS authorized for use by the second user at the second facility. Then, a selection from the first user of a first PAC for viewing one or more medical images and a selection from the second user of a second PACS for viewing one or more medical images is received. Based on the these selections, a first medical image, via the first PACS, is generated for review by the first user and a second medical image is generated, via the second PACS, for review by the second user.

BRIEF DESCRIPTION OF THE DRAWINGS

Embodiments are described in detail below with reference to the attached drawings figures, wherein:

FIG. 4 illustrates an exemplary virtual desktop infrastructure where a single PACS is configured at the registry level of a domain;

FIG. 5 illustrates an exemplary virtual desktop infrastructure where the PACS are configured at the database level allowing for use of multiple PACS within one domain;

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-storage media for computer-based medical information users to monitor an individual's risk for a second event to occur subsequent to a first event based on an analysis of pre-selected medical data elements. Following a first event, a server automatically accesses an electronic medical record store on a predetermined schedule to sample a pre-selected set of medical data elements. A logistic regression analysis is completed on the preselected set of medical data elements to generate a second risk score indicating the degree of risk that the second event will occur.

As used herein, the term facility, may be any facility which provides healthcare to an individual such as, but not limited to, a hospital, acute care facility, rehabilitation facility, urgent care facilities and the like.

Figure 1:
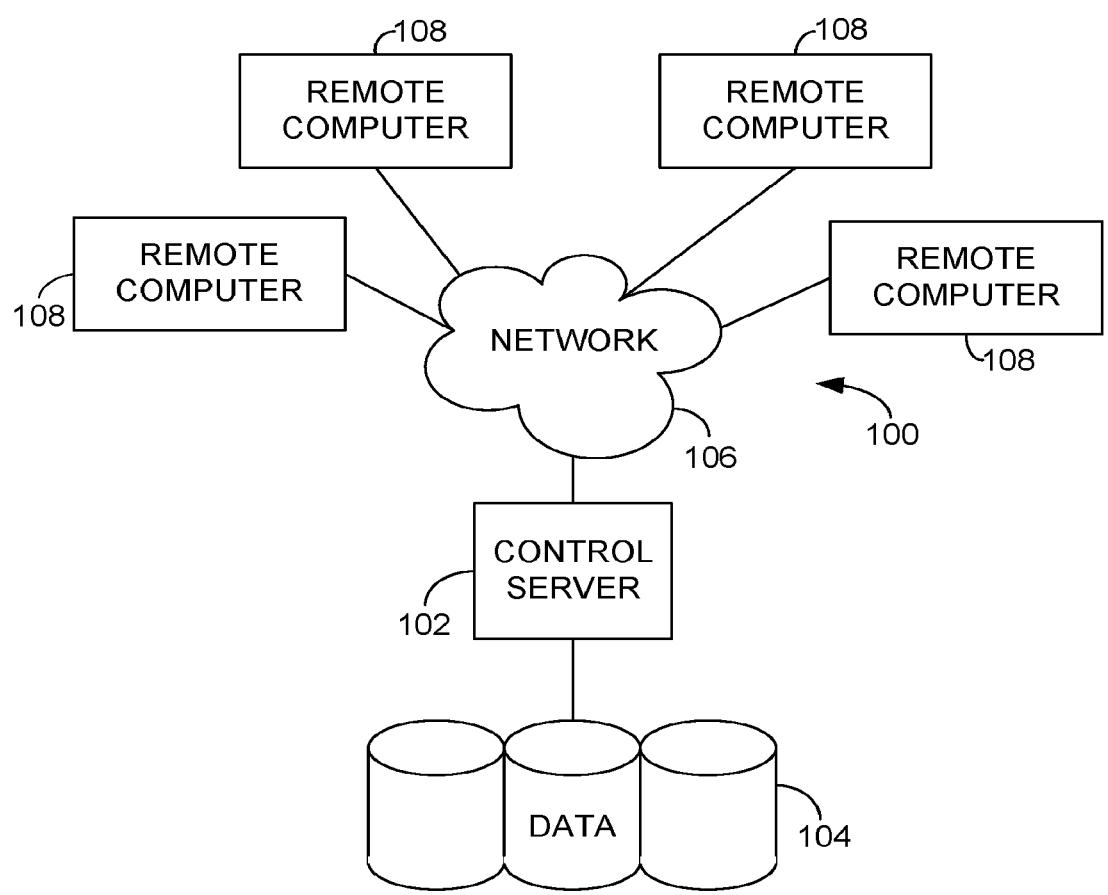
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein. It will be appreciated by those having ordinary skill in the art that the connections illustrated in FIG. 1 are also exemplary as other methods, hardware, software, and devices for establishing a communications link between the components, devices, systems, and entities, as shown in FIG. 1, may be utilized in the implementation of the present invention. Although the connections are depicted using one or more solid lines, it will be understood by those having ordinary skill in the art that the exemplary connections of FIG. 1 may be hardwired or wireless, and may use intermediary components that have been omitted or not included in FIG. 1 for simplicity's sake. As such, the absence of components from FIG. 1 should not be interpreted as limiting the present invention to exclude additional components and combination(s) of components. Moreover, though devices and components are represented in FIG. 1 as singular devices and components, it will be appreciated that some embodiments may include a plurality of the devices and components such that FIG. 1 should not be considered as limiting the number of a device or component.

The present technology might be operational with numerous other special-purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be operational and/or implemented across computing system environments such as a distributed or wireless "cloud" system. Cloud-based computing systems include a model of networked enterprise storage where data is stored in virtualized storage pools. The cloud-based networked enterprise storage may be public, private, or hosted by a third party, in embodiments. In some embodiments, computer programs or software (e.g., applications) are stored in the cloud and executed in the cloud. Generally, computing devices may access the cloud over a wireless network and any information stored in the cloud or computer programs run from the cloud. Accordingly, a cloud-based computing system may be distributed across multiple physical locations.

The present technology might be described in the context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Computer-readable media does not include signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations including operating systems, device drivers and medical information workflows. The remote computers might also be physically located in traditional and nontraditional medical/healthcare care environments so that the entire medical community might be capable of integration on the network. The remote computers might be personal computers, servers, routers, network PCs, peer devices, other common network nodes, or the like and might comprise some or all of the elements described above in relation to the control server. The devices can be personal digital assistants or other like devices. Further, remote computers may be located in a variety of locations including in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Health care providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire medical community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote medical device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
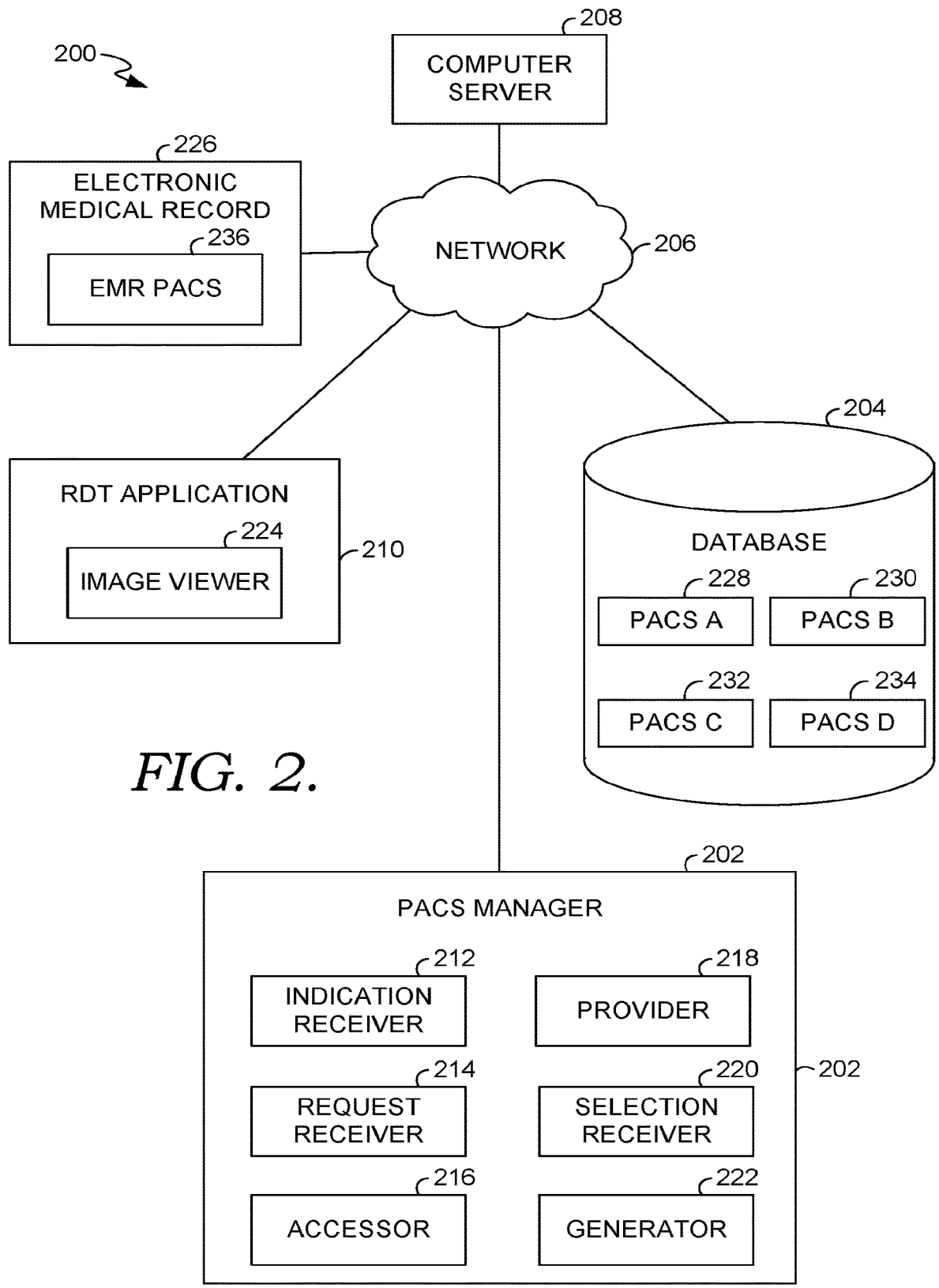
FIG. 2 is an exemplary system architecture suitable to implement embodiments of the present invention.

Turning now to FIG. 2, an exemplary computing system 200 is depicted. The computing system 200 (hereinafter "system") is merely an example of one suitable computing system and is not intended to suggest any limitation as to the scope of use or functionality of embodiments of the present invention. Neither should the system 200 be interpreted as having any dependency or requirement related to any single component or combination of components illustrated herein.

In some embodiments, one or more of the illustrated components may be implemented as a stand-alone application. The components described are exemplary in nature and in number and should not be construed as limiting. Any number of components may be employed to achieve the desired functionality within the scope of the embodiments hereof. Further, components may be located on any number of servers.

In the embodiment shown in FIG. 2, the system 200 includes a PACS manager 202, database 204, network 206, computer server 208, radiology desktop (RDT) application 210, and electronic medical record 226. While FIG. 2 illustrates only one computer server 208, it is contemplated that the system 200 may comprise any number of servers 208.

The electronic medical record 226 is comprised of in exemplary aspects, medication information, vital sign information, physician orders, demographic information, laboratory and/or procedure values and results, medical history (symptoms, diagnoses, and the like), medication history, medical procedure history, treatment history, number of readmissions and causes for readmission, social determinants (health literacy, behavioral factors, support network, and the like), assessment information for the individual, and any other pertinent medical data monitored by a healthcare system. The EMR further comprises an EMR PACS 236, which is built into the EMR. The EMR PACS 236 is available within the EMR 226 to view medical images within the EMR and report findings. Previously, users were limited to either using the EMR PACS 236 or a third party PACS, such as PACS A (228), but could not utilize both at the same time.

The RDT application 210 comprises an image viewer 224. The RDT application is utilized by a radiologist to view medical images from various radiological exams. The image viewer 224 is located within the RDT application and launches the actual medical image. As will discussed herein, a radiologist will launch the RDT application, which may be configured to communicate with a PACS so that the PACS is utilized to transmit the medical images from radiological exams to the image viewer 224 on the RDT application. The RDT application 210 may be located on any user device, such as a laptop.

As will be escribed herein, there are multiple PACS that are stored within the database 204, which allows for the use of multiple PACS by more than one facility sharing the same domain. As shown, the exemplary database comprises PACS A 228, PACS B 230, PACS C 232, and PACS D. Each PACS is stored as a key value pair and associated with one or more authorized facilities within the database 204. For example, PACS A 228 may be stored with key value pairs that indicate that PACS A is authorized for use at all facilities utilizing the domain. By contrast, PACS B 230 may only be authorized for use at a single facility. While database 204 comprises four exemplary PACS in FIG. 2, it is contemplated that the database my store as many different PACS as needed while not exceeding the database 204's storage capacity.

Generally, the PACS manager 202 is configured to allow a healthcare provider to utilized multiple PACS to view one or more medical images. In this embodiment, the PACS manager 202 is comprised of an indication receiver 212, a request receiver 214, an accessor 216, a provider 218, a selection receiver 220, and a generator 222. In this aspect, the PACS manager 202 is comprised of six subcomponents (listed above). However, in other aspects, the PACS manager 202 may be comprised of more or less components and any and all variations are contemplated herein. The components described are exemplary in nature and in number and should not be construed as limited. Any number of components may be employed to achieve the desired functionality within the scope of the embodiments hereof.

Additionally, in some aspects, the PACS manager may also be located within the database 204. It will be appreciated that some or all of the subcomponents of the PACS manager 202 may be accessed via the network 206 and may reside on one or more devices. Further, while system 200 is comprised of one PACS manager 202, it is contemplated that the system 200 may include more than one PACS manager 202. It is also contemplated that the PACS manager may be integrated into the RDT application 210.

The indication receiver 212 within the PACS manager 202 is configured to receive an indication to launch a radiology desktop application 210 on a user interface at a first facility. The indication receiver may receive the indication to launch the RDT application 210 from a healthcare provider, such as a radiologist, who needs to review one or more medical images for one or more individuals and prepare assessments and diagnoses regarding the one or more medical images. The indication received by the indication receiver 212 to launch the RDT application may be received from a user at a facility, such as a hospital. In some instances, the indication to launch the RDT may be received from a user working remotely from another location outside the facility.

The request receiver 214 receives a request from the user to utilize one or more PACS to view one or more medical images. The request receiver 214 may receive the request to utilize one or more PACS from the system 200 or a user. When a user, such as a radiologist, either at a facility or remotely needs to review medical images from radiological exams, the radiologist may launch the RDT application 210 and send a request to the system to utilize one or more PACS. In order to view the specific medical image desired, the radiologist will need to utilize a PACS to transmit the medical images to be reviewed. When the request receiver 214 receives the request from a radiologist, the request may indicate which PACS is desired to be used. Additionally, the request received by the request receiver 214 may also compromise an order number that is associated with the radiological exam and medical image to be viewed. Previously, the radiologist would have only had one PACS available for use at a facility. However, the present system allows the radiologist to be able to choose more than one PACS that are approved for use for the facility associated with the radiologist.

Next, the accessor 216 accesses the database 204 to identify one or more PACS authorized for use at a first facility. As mentioned, the system 200 allows for the use of multiple PACS on one domain for one or more facilities, which is an improvement to existing technology and removes the previous restrictions of prior systems. While more than one PACS may be utilized, not all PACS may be available for each facility on a shared domain. For example, facility A may be authorized to use PACS A 228, PACS B 230, and PACS C 232. Facility B, located on the same domain, may be authorized to use PACS B 230 and PACS C 232 only. As such, when the request receiver 214 receives the request to utilize one or more PACS to view one or more medical images, the accessor 216 that accesses the database 204 will identify only those PACS that are authorized for use at the facility associated with the request. In some aspects, a domain may be shared by multiple facilities within a large healthcare system (e.g. urban hospital system with multiple locations). In this case, each separate facility within the same healthcare system may have different authorized PACS. In other aspects, the domain may be shared by multiple different facilities that have no relationship with one another. Therefore, based on the location from where the request receiver 214 receives the request to utilize one or more PACS from a first user, the accessor 216 will access the database 204 and identify the one or more authorized PACS available for the particular facility location.

Once the accessor 216 has identified the one or more PACS authorized for use at a first facility, the provider 218 will provide the first user, via the first user interface of the RDT application, with a first PACS authorized at the first facility. To do this, the provider 218 will provide a first PACS for selection on the first user interface. For example, if the radiologist has requested to use PACS A at the first facility and the accessor 216 has identified that PACS A is authorized for the first facility, then the provider 218 will provide PACS A for use by the radiologist at the first facility on a user interface. In some aspects, the first user may be presented with the option to use PACS A via the RDT application. In other aspects, the first user may be utilizing the EMR to address requests for reviewing medical images and as such, the PACS approved for the first facility may be provided via the EMR on the user interface. It is further contemplated that, in yet other aspects, the EMR itself may have an EMR specific PACS that may have been requested by the first user and authorized for use at the first facility. Additionally, where the first facility is authorized for the use of more than one PACS, the provider 218 will provide the first user, via the RDT application, a second authorized PACS for use. As such, the first user may be provider with two or more PACS for use. In this case, the first user will have the capability to choose which PACS the user wants to use to view the medical images and has the ability to toggle back and forth between the first PACS and the second PACS to view different medical images. For example, if PACS A is the first PACS authorized for use and PACS B is the second PACS authorized for use, then provider 218 may provide both PACS A and PACS B to the first user for use. The first user can select which PACS is optimal for reviewing the necessary medical images or the user may decide to utilize both PACS A and PACS B to view different types of medical images (e.g. CT scan versus mammogram). In that case, the first user may review certain types of images on PACS A and others on PACS B. Additionally, the PACS will utilize the order number associated with the radiological exam and medical image to be viewed to search for and provide the medical image for viewing on the RDT application 210.

After the first PACS and second PACS are provided to the first user by the provider 218, the system 200 will generate, via generator 222, a first medical image, via the first PACS, for review by the first user. The generator 222 will also generator a second medical image, via the second PACS provided by the provider 218 for use by the first user at the first facility. Once the first medical image and the second medical images are reviewed by the first user, the first user will generate analysis reports for each medical image. When the system 200 receives each analysis report, the system may store the report in the database 204 or EMR 226. The results of each analysis report will be communicated to the EMR 226 so that the appropriate treatment can be determined for each individual associated with each medical image reviewed.

Additionally, in instances where the user or radiologist is working remotely and may need to review medical images from another location, providing the first user with a first PACS and a second PACS authorized for the first user will allow the radiologist choice regarding which PACS is optimal for the circumstance. For example, certain PACS may be more user-friendly for use on a cell phone while other PACS may be more user friendly on a desktop via the RDT application.

It is also contemplated that in situations where a radiologist may be associated with more than one facility on the shared domain, the provider 218 may also provide the radiologist with multiple PACS for use so that the radiologist is able to review medical images from more than one facility via the same RDT application. In other words, if the radiologist requesting the use of more than one PACS is working at two facilities within a domain, the provider 218 can provide the radiologist with different PACS, via the RDT application, for each facility.

In some aspects, the system 200 will receive requests from more than one user at either the same or a different facilities within the shared domain. Unlike previous systems, the present system will allow the different users at different facilities to use different PACS, thereby not limiting the PACS available for use in a single domain. In such embodiments, the indication receiver 212 may receive a first indication to launch a RDT application on a first user interface associated with a first facility (e.g. the first user interface is located at the first facility or the first user is working remotely, but the first user's device is associated with the first facility). The indication receiver 212 will also receive a second indication to launch a RDT application on a second user interface at a second facility. Based on receiving these indications, the request receiver 214 will receive a first request from the first user to utilize one or more PACS to view one or more medical images. The request receiver will also receive a second request from a second user to utilize one or more PACS to view one or more images at the second facility. Then, the accessor 216 will access the database to identify one or more PACS authorized for use at each of the first facility and the second facility. Based on the identification of the PACS authorized for each facility, the provider 218 will provide the first user with one or more PACS authorized for use at the first facility. Additionally, the provider 218 will provide the second user with one or more PACS authorized for use at the second facility.

In this example, once the first user is provided with one or more PACS authorized for use at the first facility, the first user can make a selection as to which PACS the first user would like to utilize to review the medical images. When this occurs, the selection receiver 220 will receive a selection of a first PAC from the first user for viewing one or more medical images. The first user may be provided with a drop down menu where the first user can select one or more PACS to use that are provided by the provider 218 based on being authorized for the first facility. Similarly, the selection receiver 220 receives a selection of a second PACS for viewing one or more medical images from the second user.

Once the first and second PACS selections are received by the selection receiver 220, the generator 222 will generate a first medical image, via the first PACS, for review by the first user and a second medical image, via the second PACS, for review by the second user. Once the first user and second user view the first medical image and the second medical image, each user can analyze the medical image from the associated radiological exam and provide the necessary assessment or diagnosis, which will be input into the EMR 226 for the use of other healthcare providers in treating the individuals who underwent the radiological exam.

Figure 3:
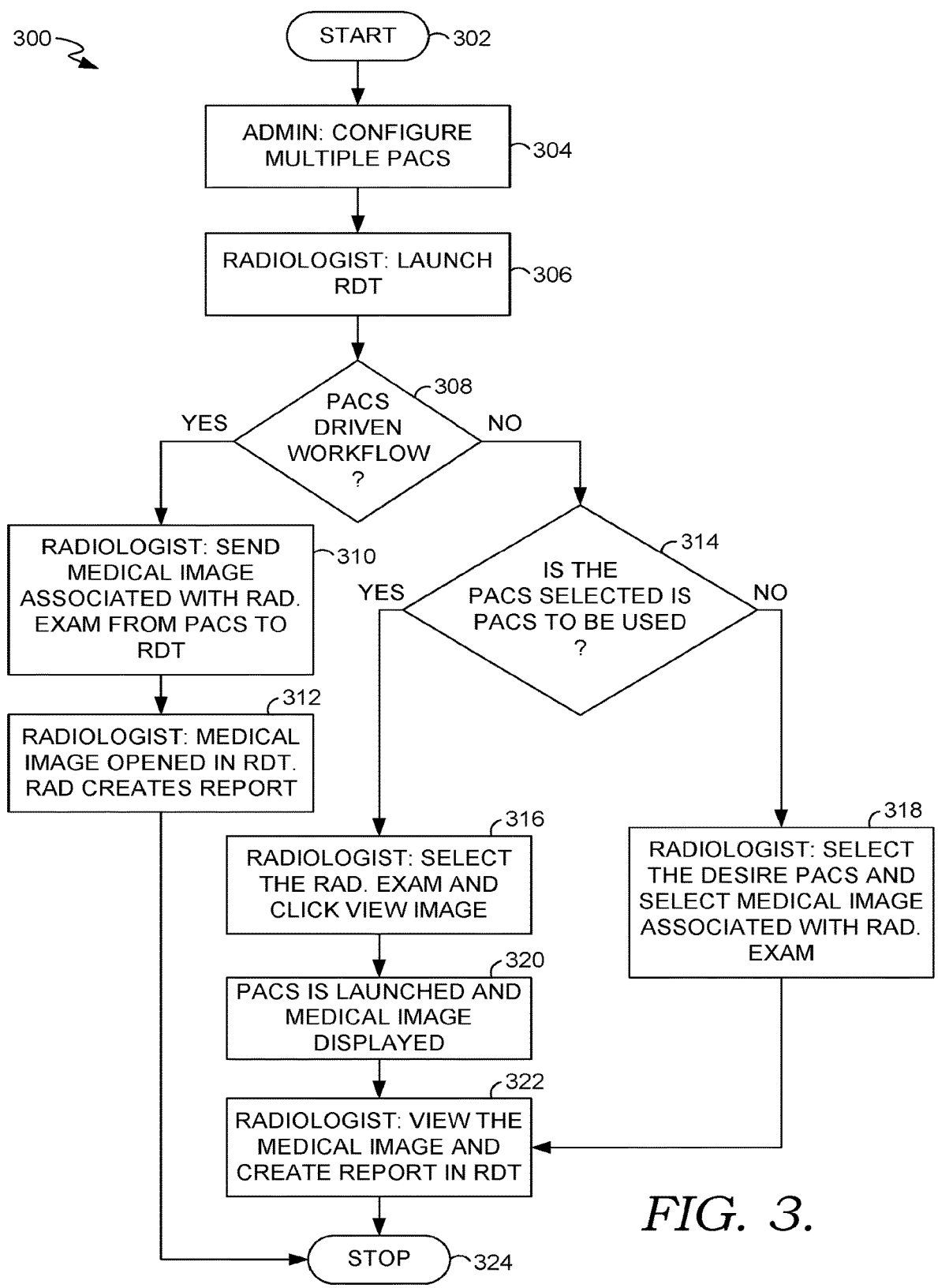
FIG. 3 illustrates an exemplary system workflow illustrating implementation of embodiments of the present application.

Turning next to FIG. 3, an exemplary system workflow of utilizing multiple PACS to view one or more medical images is illustrated. The process starts at block 302. As discussed herein, the present system provides for configuration of multiple PACS for a given domain comprising one or more facilities at block 304. The PACS are configured at the database level to allow for the use of multiple PACS by one user within a facility on a domain or multiple users at different facilities within the same domain (e.g. multi-tenant domain). After multiple PACS are configured, the radiologist launches the RDT application 210 at block 306. The RDT application 210 may be launched on any user interface, including, but not limited to laptops, desktops, tablets, cellular devices, and the like.

At block 308, the system 200 will determine whether or not the workflow is PACS driven based on the PACS that is selected by the user. Prior to this, the accessor 216 accesses the database to determine which PACS s are authorized for use at the specific facility by the user and the provider 218 provides the authorized one or more PACSs to the user for selection (e.g. multiple PACSs are available for selection in a drop down menu). When the selection receiver 220 receives the selection from the user for the PACS to be used, the PACS selected can either be unidirectional or bidirectional as shown in FIG. 5. If the PACS selected is unidirectional, it means that the communication and requests can only occur from the PACS to the RDT application 210. If the PACS selected is bidirectional, then the communication can be two ways—from the RDT application 210 to the PACS and from the PACS to the RDT application 210.

If it is determined that the PACS selected is a unidirectional PACS (e.g. PACS B from FIG. 5), then the PACS is PACS driven (e.g. communication can only occur from the PACS to the RDT application 210). In this case, the radiologist will send the medical image associated with a radiological exam being viewed from the PACS selected to the RDT application 210 at block 310. Then, at block 312, the radiologist will open the medical image in the RDT application and create the necessary report. Once the report is complete, the process ends at 324. After this, the radiologist will move onto the next radiological exam and associated medical image for viewing and reporting via the same or a different authorized PACS.

On the other hand, if the PACS selected by the user is determined not to be PACS driven (e.g. the PACS is a bidirectional PACS such as PACS A in FIG. 5) at block 308, then the system 200 will determine whether the PACS selected is the PACS to be used at 314. If the PACS selected is not the PACS to be used, then the radiologist will select the desired PACS and selected the radiological exam and associated medical image to be viewed and view it at 318. The PACS selected by the radiologist will be another bidirectional PACS that is authorized for use at the facility associated with the radiologist. When this occurs, an order ID is sent from the PACS to the RDT application to search for the image to be reported. Then, the radiologist will view the medial image and create a report in the RDT application 210 at 322. Once completed, the process ends at 324 and the radiologist can move onto the next radiological exam and associated medical image to be reviewed. In the future, the selected PACS can be saved as the default to be used for the next time. For example, if the radiologist selected PACS A 228 for use, then PACS A 228 may be the default selection for the next medical image to be viewed.

By contrast, if the PACS selected is the PACS to be used at 314, then the radiologist will selected the specific radiological exam for which an image is to be viewed at 316. A this time, the RDT application 210 sends a request to the PACS along with an order ID for the exam so that the PACS can search for the specific exam within a PACS database. Once located, the PACS will be launched and the medical image will be displayed at 320 in the image viewer 224 (e.g. the PACS viewer). Then, the radiologist will view the image and create a report in the RDT application 210 at 322. The report created by the radiologist stays in the RDT application 210 while the requests to open the images stays with the PACS. Once the image has been viewed and the report is completed, the process ends at 324.

Next, FIG. 4 illustrates the way PACS have been historically configured at the registry level. An exemplary virtual desktop infrastructure (VDI) 400 is shown. The VDI 400 is a hosting of desktop environments on a central server and is a form of desktop virtualization. As discussed, PACS have been configured at the registry at the domain server, which meant that only one PACS could be configured for each domain. As shown in FIG. 4, the VDI 400 configuration interface comprises multiple fields of data. The first field, 402 indicates the name of the PACS that is configured to the system 200. In FIG. 4, the PACS configured is PACS A. Additionally, the VDI Mode 404 is shown as being bi-directional, meaning that communication can occur from the RDT application 210 to the selected PACS and vice versa. In other aspects, the VDI mode may be uni-direction, meaning that the communication can only occur from the PACS to the RDT application 210. Further, the VDI 400 configuration interface also includes an order ID 408, which is an identification code associated with the medical image or radiological exam to be reviewed. The pathway 410 location for the specific PACS is also shown. The facility 414 is shown as a drop down selection and lists the facilities within the domain. As shown, all facilities are selected, meaning that facilities 1-8 are authorized to use PACS A. However, there is only one PACS, PACS A, that is authorized for use on this domain. As such, every user at each facility 1-8 within the domain may only utilize PACS A to view medical images.

By contrast, FIG. 5 illustrates the implementation of the present disclosure that allows for the use of multiple different PACSs by multiple facilities within one domain. As shown, VDI 500 comprises the following fields: name 502, VDI mode (bidirectional or unidirectional) 504, VDI data 506, Order ID 508, the pathway location 510 and facility 512. Unlike FIG. 4, where the PACS was configured at the registry level, in FIG. 5, each PACS authorized for each facility is stored separately as a key value within the database 204. This allows for different facilities within the same domain to use different PACS s and for users at one facility to utilize more than one PACS for reviewing medical images or different users at different facilities within the same domain to utilize more than one PACS. As such, each facility has one or more PACS that are authorized for use. As shown in FIG. 5, there are three PACSs that have been added and available for use for this particular domain, PACS A 516, PACS B 518, and PACS C 520. For PACS A 516, the VDI mode 504 selected is bi-directional and the system 200 has approved all facilities to use PACS A. As such, communication may occur from the RDT application 210 to the PACS A 516 and vice versa. Therefore, different users at each facility will be able to utilized PACS A to view images via the RDT application 210.

Additionally, PACS B 518 has been selected to have a VDI mode 504 that is unidirectional and is approved for use in facilities 1, 2, 3. PACS C 520 has been selected to have a bidirectional VDI mode 504 and is approved for use facilities 4, 5, and 6. Additionally, as seen in FIG. 5, the option to add an EMR PACS 522 is also available. As such, the system 200 may be configured to not only use third party PACSs such as PACS A-C, but also the EMR PACS 236 offered via the EMR 226. The VDI 500 demonstrates how multiple PACSs are available for use at different facilities within the same domain. Not all the facilities have received approvals to use all the PACSs. However, the new VDI 500 shown in FIG. 5 allows for greater flexibility for users. For example, a radiologist at facility a can choose to use PACS A or B or both, depending on the radiologists preferences and medical image to be viewed. At the same time, a radiologist associated with facility 4 can choose to use PACS A or PACS C or both.

Figure 6:
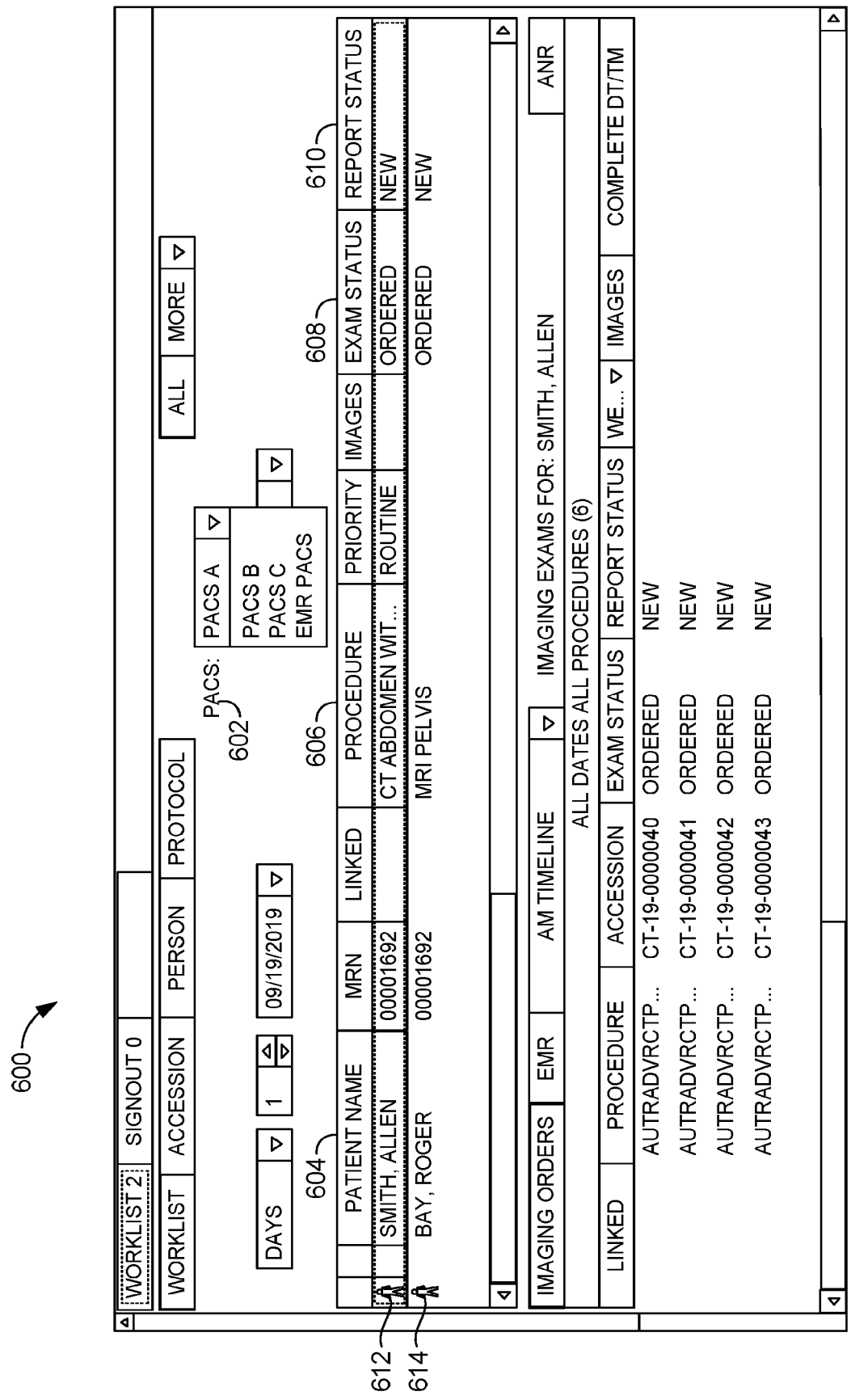
FIG. 6 illustrates an exemplary radiologist desktop application configured for multiple PACS use.

Next, FIG. 6 illustrates the implementation of VDI 500 in an exemplary RDT application 600 on a radiologist's user interface. As shown, the RDT application 210 includes several informational fields such as the PACS type 602 (which includes a drop down menu to select the desired PACS), patient name 604, the procedure 606, the exam status 608, and the report status 610. The radiologist has two patient names 604 whose medical images need to be reviewed. The first patient, Allen Smith 612's procedure 606 to be reviewed is a CT of the abdomen with contrast. The second patient, Roger Bay 614's procedure 606 to be reviewed is an MRI of the pelvis. As seen on the RDT application, the radiologist can choose which PACS type 602 to utilize to view each of medical images. PACSs A-D and EMR PACS are authorized and available to use. As such, the radiologist may select the same PACS (e.g. PACS A) or two different PACSs (e.g. PACS A and EMR PACS) to review the two different medical images for Allen Smith and Roger Day.

Figure 7:
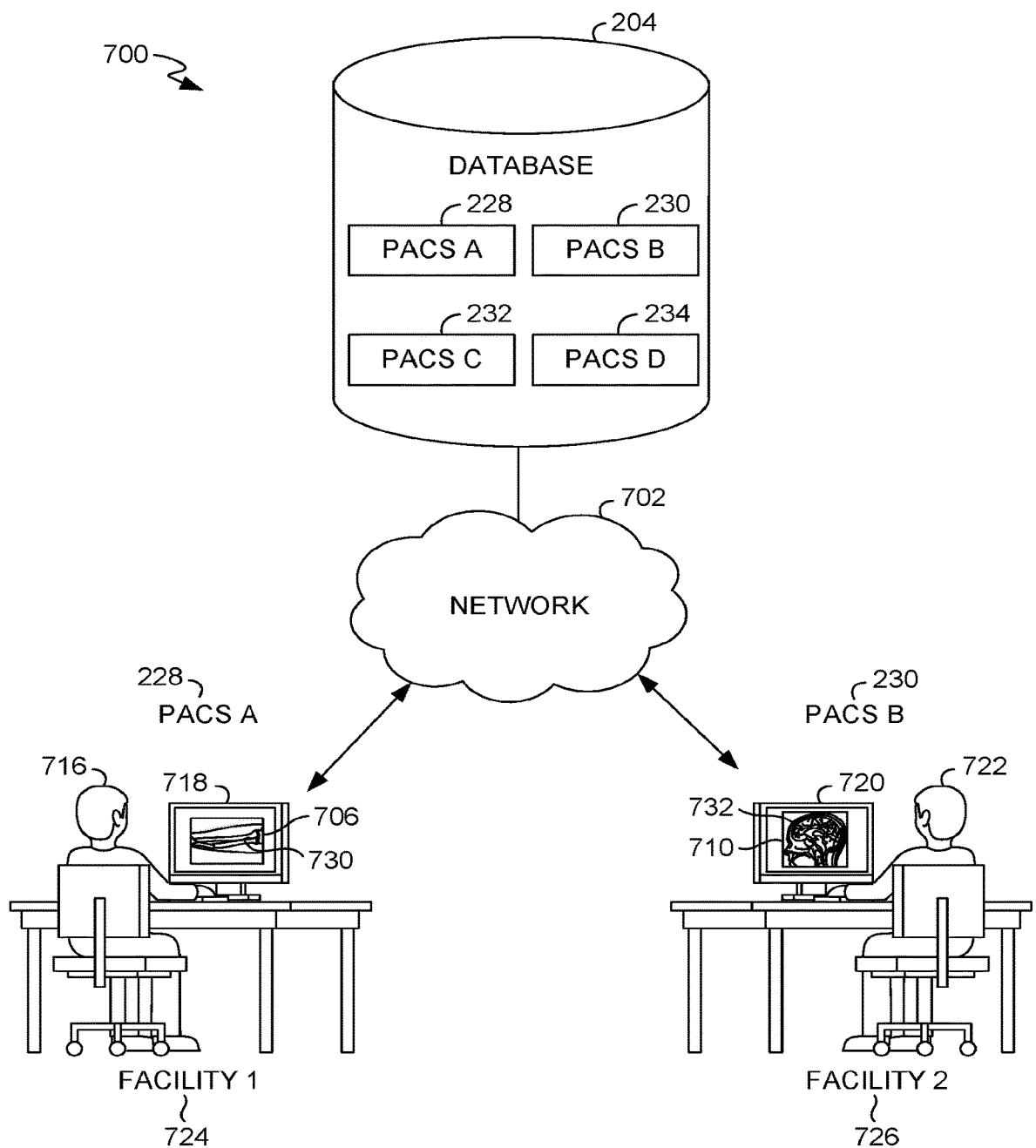
FIG. 7 illustrates the use of multiple PACS by different users at different facilities sharing the same domain.

FIG. 7 further illustrates an exemplary system 700 in which multiple PACSs are available and authorized for users at multiple facilities. As shown, database 204 has four PACSs configured to it. Each PACS is configured to capture, store, and display one or more medical images on user interfaces. Each of PACS A 706, PACS B 708, PACS C 710, and PACS D 712 have been identified by the accessor 216 as authorized for use at the first facility 724 and the second facility 726. In this example, a first radiologist 716 is working from a first facility 724 and utilizing a first RDT application 706. A second radiologist 722 is working from a second facility 726 and utilizing a second RDT application 710. In this example, the indication receiver 212 has received an indication from the first radiologist 716 to launch the first RDT application 706 on the first user's interface 718 and the request receiver 214 has received a first request from the first radiologist 716 to utilize one or more PACSs to view one or more medical images. Based on such a request, the accessor 216 accessed the database 204 to identify one or more PACS that are authorized for use at the first facility 724. The provider 218 then provides the first radiologist 716 with one or more PACS authorized for use by the first radiologist 716 at the first facility 724. As shown, the first radiologist 716 has selected PACS A to be used on the first user interface 718 and the selection receiver 220 will receive the selection. Also, as shown with the two directional arrow, PACS A 228 is a bi-directional PACS. Based on this, the generator 222 will generate, a first medical image 730, via PACS A 228, for review by the first radiologist 716. In this instance, the first medical image 730 to be reviewed by the first radiologist 716 is an x-ray of a bone. Upon receiving the first medical image 730, the first radiologist 716 will review the second medical image 730 and make the appropriate assessment/diagnosis and then generate a report accordingly. The report generated will be either directly input into the EMR 226 or communicated to the EMR 226 for use in treatment of the individual who underwent the x-ray.

The same process will take place for the second radiologist 722 at the second facility 726. After the second radiologist 722 selects bidirectional PACS B 230 from the authorized PACSs provided by the provider 218 for the second facility 726 and the selection receiver 220 receives the selection of PACS B 230, the generator 222 will generate a second medical image 732, via PACS B 230, for review by the second radiologist 722. In this case, the second medical image 732 is a CT scan of the brain. As shown, by configuring the PACSs to be stored at the database 204 instead of at a registry within the system 200, both the first radiologist 716 and the second radiologist 722, who share one domain, are able to utilize different PACSs for review and analysis of medical images.

Figure 8:
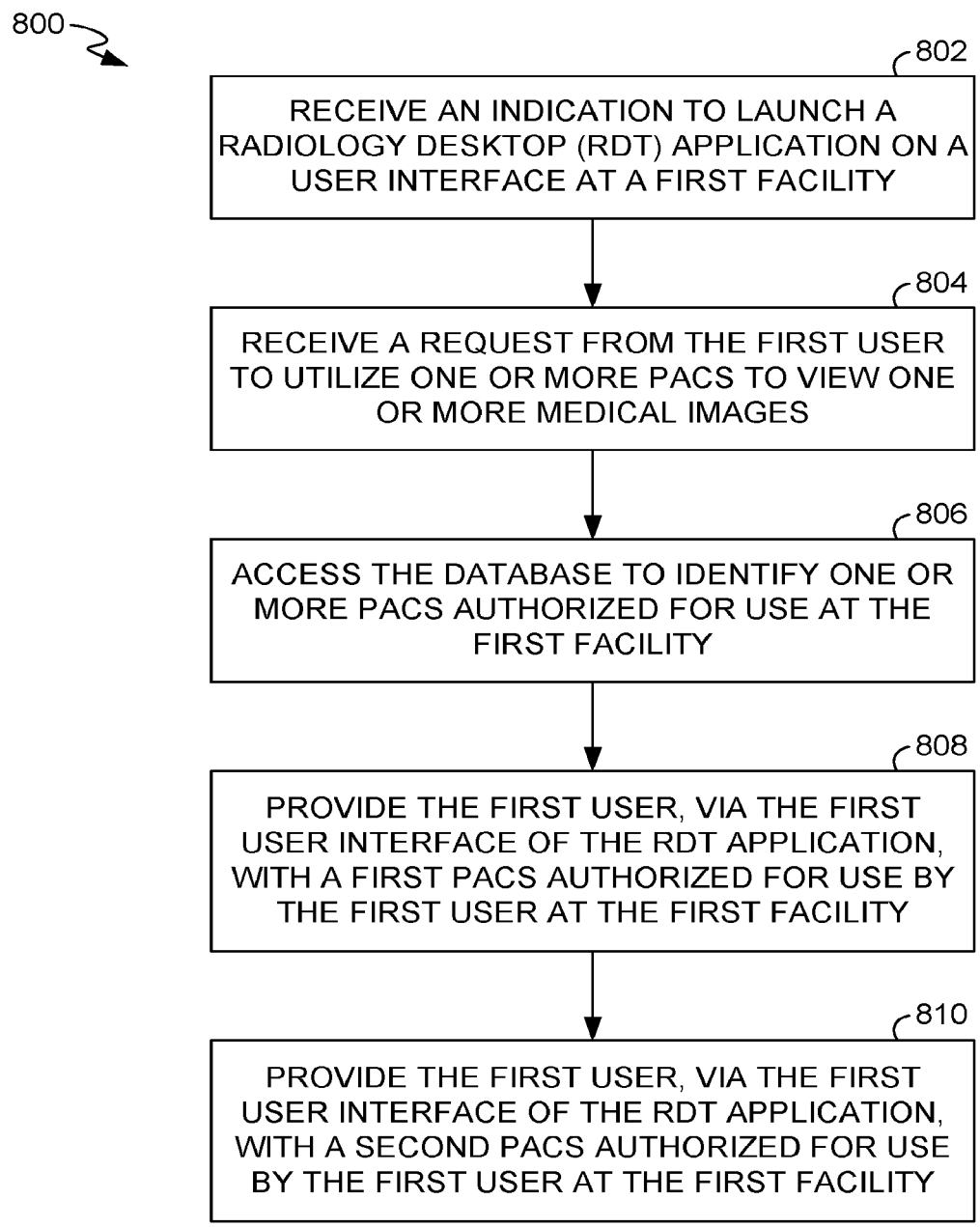
FIG. 8 is a flow diagram describing an exemplary method of executing embodiments of the present invention.

FIG. 8 illustrates a flow diagram showing an exemplary method 800 of executing embodiments of the present invention. Beginning with block 802, an indication is received by the indication receiver 212 to launch a radiology desktop application on a user interface at a first facility. At block 804, the request receiver 214 receivers the request from the first user to utilize one or more PACSs to view one or more medical images. As discussed, the first user may request to view the one or more medical images via the RDT application 210 on a user desktop or via the EMR 226. After receiving the request, the accessor 216 accesses the database 204 to identify one or more PACS authorized for use at the first facility at block 806. In aspects, all facilities may be authorized to use all configured PACSs while in other instances, certain facilities may be authorized to use certain PACSs while others are not. Then, at block 808, the provider 218, provides, via the first user interface of the RDT application 210, a first PACS authorized for use by the first user at the first facility at block 810. At block 810, the provider 218 will provide the first user, via the first user interface of the RDT application 210, with a second PACS authorized for use by the first user at the first facility.

Figure 9:
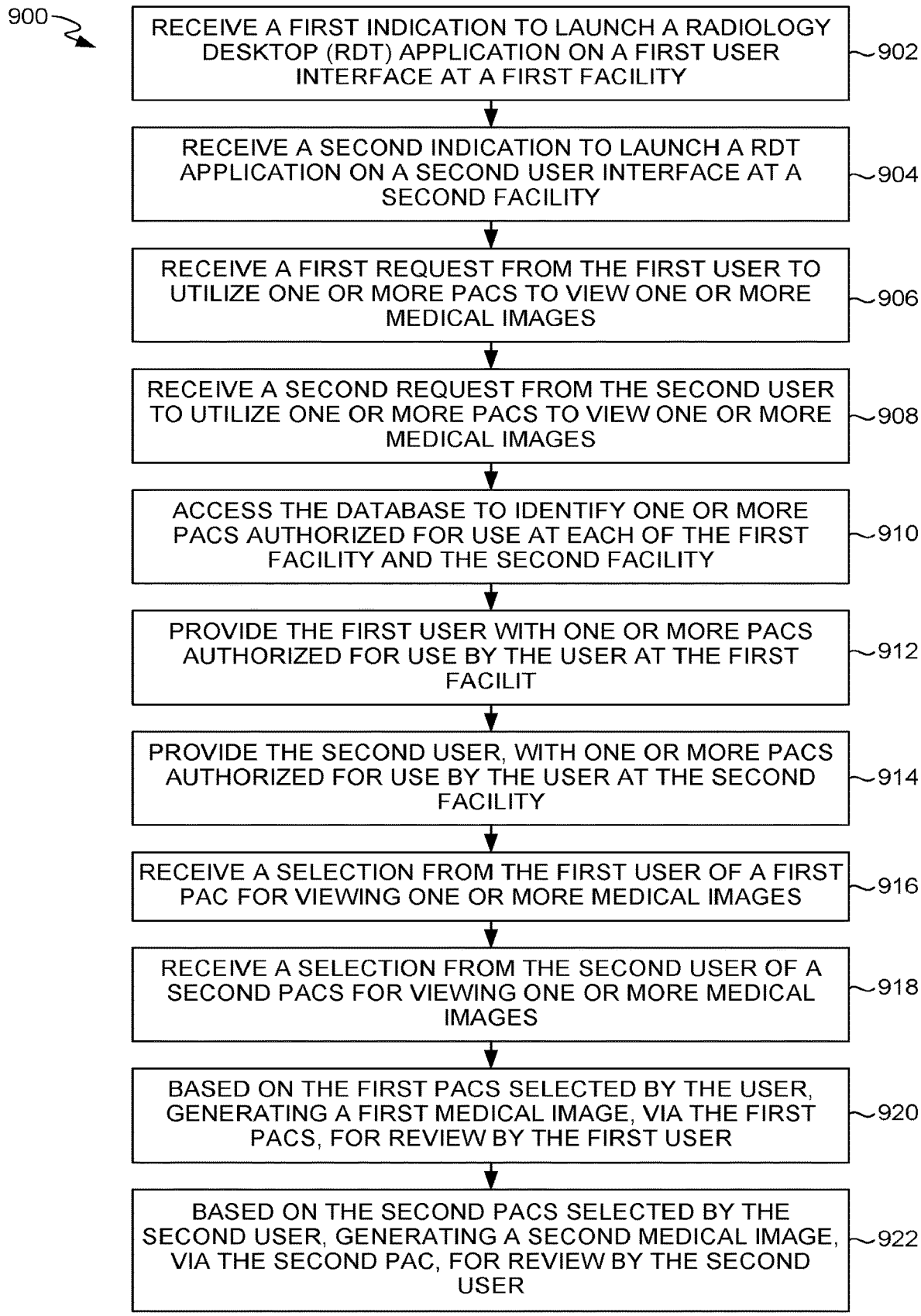
FIG. 9 is a flow diagram describing another exemplary method of executing embodiments of the present invention.

FIG. 9. illustrates a flow diagram depicting another exemplary method 900 of executing embodiments of the present invention. In the method 900 illustrated in FIG. 9, two different users at two different facilities are utilizing the same domain. As such, the two users may request the same or different PACS to view medical images and each facility may be authorized to use the same or different PACS. Beginning with block 902, the indication receiver 212 receives a first indication to launch a radiology desktop application on a first user interface at a first facility. Then, the indication receiver 212 receives a second indication to launch an RDT application on a second user interface at a second facility at block 904. In this aspect, the first user and second users are located at a first and second facility. It is contemplated that the first facility and the second facility may be facilities within the same healthcare system. For example, the first facility might be an urgent care/emergency department facility and the second facility might be a hospital. The first facility and second facility may or may not be physically attached or adjacent to one another. Additionally, it is contemplated that in other aspects, the first facility and the second facility may not have any connection to one another. For example, in rural areas, the first facility may be a first community hospital located in a first small town and the second facility may be a second community hospital located in a second small town several hundreds of miles away. The two facilities may share the same domain in order to be cost efficient. However, each facility may have different needs and capabilities with regard to radiological examinations and as such, each facility may want to utilize different PACS s for viewing medical images.

Once the first indication and the second indications to launch RDT application 210 on each user's interface are received, the request receiver 214 receives a first request from the first user to utilize one or more PACS to view one or more medical images at block 906. Then, at block 908, the request receiver 214 receives a second request from the second user to utilize one or more PACSs to view one or more medical images. Each user may request to utilize one or more PACSs based on user preference or based on the type of medical image to be viewed.

Next, the accessor 216 accesses the database to identify one or more PACSs authorized for use at each of the first facility and the second facility at block 910. As previously mentioned, each facility located on the same domain may not be authorized to utilize each PACS available. As such, even if a user requests to use a PACS, the system 200, will need to determine whether the specific PACS requested is authorized for the facility. Since different facilities may be authorize to use different PACS s, the accessor 216 will identify different PACS authorized for each facility.

Once the accessor 216 has accessed the database 204 and identified the PACS authorized for use at the first facility and the second facility, the provider 218 will provide the first user with one or more PACSs authorized for use by the first facility at block 912. The provider 218 will also provide the second user with the one or more PACS authorized for use at the second facility at block 914. After providing the authorized PACS to the first user and the second user, the selection receiver 220 receives a selection from the first user of a first PACS for viewing one or more medical images at block 916. The selection receiver 220 also receives a s selection from the second user of a second PACS for user by the user at the second facility at block 918.

Then, based on the first PACS selected by the first user, the generator 222 will generate a first medical image, for review by the first user at the first facility at block 920. At block 922, the generator 222 will generate a second medical image for review by the second user based on the second PACS selected by the second user. The first and second users may then review each medical image and provide the appropriate reporting via the RDT Application 210. The report generated by the first and second users may be stored in the database 204 or communicated to the EMR 226.

While block 902-922 present the method in order discussed above, it is contemplated that the system 200 may receive the indications and requests from the first user at the first facility and the second user at the second facility simultaneously. As such, the system 200 may provide the both the first user and the second users with the PACS s authorized for each facility at the same time and then, in response, to the selections made by each user, generator the medical images for review by each user simultaneously. System 200 is adaptable and intelligent and as such, the presented method is exemplary and variations in the order are contemplated herein.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A dynamic system comprising:
   one or more processors configured to:
      transmit a medical image to a corresponding RDT application at different locations based on multi-user requests to utilize multiple Picture Archiving Communication Systems (PACS);
      determine that the multiple PACS are stored on a shared domain;
      determine whether each of the multiple PACS is authorized for use at each of the different locations; and
      provide a plurality of users of the corresponding RDT application at different locations concurrent access to one or more of the multiple PACS to access the medical image based on authorization determinations.

2. The system of claim 1, wherein one or more databases are accessed to determine whether each of the multiple PACS is authorized for use at each of the different locations.

3. The system of claim 1, wherein the system further generates the medical image for review by the plurality of users.

4. The system of claim 3, wherein the system receives at least one analysis report from one of the plurality of users for the medical image viewed.

5. The system of claim 1, wherein the system further stores the analysis report in one or more of the databases.

6. The system of claim 1, wherein the multi-user requests to utilize the multiple PACS each include an order number associated with the medical image.

7. The system of claim 1, wherein the multiple PACS authorized for use are unidirectional.

8. The system of claim 1, wherein the multiple PACS authorized for use are bidirectional.

9. The system of claim 1, wherein the system further transmits the analysis report for incorporation into an electronic medical record for an individual.

10. A method carried out by a server to utilize multiple Picture Archiving Communication Systems (PACS) to view radiology images, the method comprising:
    transmitting a medical image to a corresponding RDT application at different locations based on multi-user requests to utilize multiple Picture Archiving Communication Systems (PACS);
    determining that the multiple PACS are stored on a shared domain;
    determining whether each of the multiple PACS is authorized for use at each of the different locations; and
    providing a plurality of users of the corresponding RDT application at different locations concurrent access to one or more of the multiple PACS to access the medical image based on authorization determinations.

11. The method of claim 10, further comprising generating at least one analysis report for the medical image.

12. The method of claim 11, further comprising storing the at least one analysis report for the medical image in the database.

13. A dynamic system useful in a computer healthcare system that allows a healthcare provider to utilize multiple Picture Archiving Communication Systems (PACS) to view one or more medical images, the system comprising:
    a database comprising one or more PACS configured to capture, store, and display one or more medical images on one or more user interfaces associated with one or more facilities;
    one or more processors; and
    a storage device storing a computer program product comprising computer instructions that, upon execution by the one or more processors, cause the one or more processors to perform operations comprising:
    receiving a first request from a first user to utilize multiple PACS to transmit medical images to a RDT application on a first user interface at a first facility;
    receiving a second request from a second user to utilize multiple PACS to transmit medical images to a RDT application on a second user interface at a second facility;
    determining that the multiple PACS are stored on a shared multi-tenant domain and associated with a common key value pair;
    based on the common key value pair, determining whether each of the multiple PACS are authorized for use at the first facility and the second facility;
    based on determining the multiple PACS authorized for use at the first facility and the second facility, providing the first user at the first facility and the second user at the second facility with concurrent access to one or more of the multiple PACS to access the medical images
    receiving a selection from the first user of one of the multiple PACS for viewing the medical images; and
    receiving a selection from the second user of one of the multiple PACS for viewing the medical images.

14. The system of claim 13, wherein the selection of one of the multiple PACS by the first user is saved as a default PACS selection for future use.

15. The system of claim 13, wherein the selection of one of the multiple PACS by the second user is saved as a default PACS selection for future use.

16. The system of claim 13, wherein the first user and the second user select the same PACS.

17. The system of claim 13, wherein the first user and the second use select different PACS.

18. The system of claim 13, wherein the first facility and the second facility are part of a multi-tenant domain.

19. The system of claim 13, wherein the first user generates a report for each medical image viewed and the second user generates a report for each medical image medical image viewed.

20. The system of claim 19, wherein each report generated is transmitted to an electronic medical record.

* * * * *